US011419706B2

(12) United States Patent
Suter et al.

(10) Patent No.: US 11,419,706 B2
(45) Date of Patent: Aug. 23, 2022

(54) FIXATION PIN

(71) Applicant: STRAUMANN HOLDING AG, Basel (CH)

(72) Inventors: Edmund Suter, Niederdorf (CH); Steffen Kühne, Möhlin (CH); Patrick Streff, Weil am Rhein (DE)

(73) Assignee: STRAUMANN HOLDING AG, Basel (CH)

(*) Notice: Subject to any disclaimer, the term of this patent is extended or adjusted under 35 U.S.C. 154(b) by 339 days.

(21) Appl. No.: 16/453,205

(22) Filed: Jun. 26, 2019

(65) Prior Publication Data
US 2019/0314120 A1  Oct. 17, 2019

Related U.S. Application Data

(60) Division of application No. 15/446,945, filed on Mar. 1, 2017, now Pat. No. 10,376,342, which is a division
(Continued)

(30) Foreign Application Priority Data

Dec. 1, 2008 (EP) ..................................... 08020837

(51) Int. Cl.
*A61C 8/00* (2006.01)
*A61C 1/08* (2006.01)
*A61B 90/92* (2016.01)

(52) U.S. Cl.
CPC .............. *A61C 8/009* (2013.01); *A61B 90/92* (2016.02); *A61C 1/084* (2013.01); *A61C 8/0089* (2013.01); *A61C 2201/002* (2013.01)

(58) Field of Classification Search
CPC ....... A61C 8/0089; A61C 8/009; A61C 1/082; A61C 1/084; A61B 90/92
See application file for complete search history.

(56) References Cited

U.S. PATENT DOCUMENTS 3,842,824 A * 10/1974 Neufeld ............. A61B 17/8863
                                                606/309
3,885,313 A *  5/1975 Kikuchi ................. A61C 13/12
                                                433/213
(Continued)

FOREIGN PATENT DOCUMENTS

JP          63-275335 A      11/1988
JP         2001-218776 A      8/2001
(Continued)

OTHER PUBLICATIONS

Marchack, Christopher B., CAD/CAM-Guided Implant Surgery and Fabrication of an Immediately Loaded Prosthesis for a Partially Edentulous Patient, Journal of Prosthetic Dentistry, Jun. 2007, vol. 97, Iss. 6, pp. 389-394.
Kan, et al., Computer-Guided Implant Treatment with All-on-four Immediate-Function Concept, Contemporary Esthetics, Dec. 2007, pp. 20-25.
Nobel Biocare Annual Report 2005, pp. 1-107 (D6).
(Continued)

*Primary Examiner* — Si Ming Ku
(74) *Attorney, Agent, or Firm* — Oliff PLC

(57) ABSTRACT

A fixation pin for fixing a dental drill template. The fixation pin has a head having a bearing surface that is intended to bear at least partially on the drill template, or a sleeve provided in the drill template. The fixation pin has a rod having a shape of an essentially circular cylinder and extending from the bearing surface at an essentially right angle. The rod is intended to be inserted into the drill template or the sleeve provided in the drill template.

10 Claims, 5 Drawing Sheets

Related U.S. Application Data of application No. 14/617,327, filed on Feb. 9, 2015, now abandoned, which is a continuation of application No. 12/627,270, filed on Nov. 30, 2009, now abandoned.

(56) References Cited

U.S. PATENT DOCUMENTS

| | | | |
|---|---|---|---|
| 4,941,827 | A | 7/1990 | Mack |
| 5,030,092 | A | 7/1991 | Cokeley |
| 5,538,424 | A | 7/1996 | Gelb |
| 5,672,178 | A * | 9/1997 | Petersen ............... A61B 17/68 606/75 |
| 6,007,539 | A | 12/1999 | Kirsch et al. |
| 7,033,363 | B2 | 4/2006 | Powell |
| 2002/0137003 | A1 | 9/2002 | Knapp |
| 2004/0259051 | A1 | 12/2004 | Brajnovic |
| 2006/0223029 | A1 | 10/2006 | Berger |
| 2008/0057475 | A1 | 3/2008 | Feith |
| 2008/0071382 | A1 | 3/2008 | Kumar et al. |
| 2008/0118892 | A1 | 5/2008 | Adams |
| 2008/0293013 | A1 | 11/2008 | Lussi et al. |
| 2008/0293016 | A1 | 11/2008 | Lussi et al. |

FOREIGN PATENT DOCUMENTS

| | | |
|---|---|---|
| JP | 2003-063181 A | 3/2003 |
| JP | 2007-010592 A | 1/2007 |
| WO | 03/055407 A1 | 7/2003 |
| WO | 2008009080 A1 | 1/2008 |

OTHER PUBLICATIONS

Maia, B.G.F., et al., Cirurgia livre de retalho com funcao imediata associada ao planejamento computadorizado relato de case clincico. Rev. Dental Press Periodontia Implantol., Maringa, 2(2), Apr./May/Jun. 2008, pp. 11-109 (DS).
NobelPSeedy TM Groovy TM Shorty TM, procedures & products—Powered by Procera, 2008, Nobel Biocare Services AG, Sweden, pp. 1-44 (D9).
Office Action dated Nov. 6, 2013 by the Japanese Patent Office citing JP 63-275335.
European Search Report issued in corresponding EP No. 08020837.4-2318 dated May 20, 2009.
Inclusive Magazine, Restorative Driven Implant Solution, vol. 1, Issue 4, pp. 1-4 and pp. 42-52, 2009.
Dent. Today, Feb. 2002, vol. 21, No. 2, pp. 106-111.
NobelReplace TM Tapered, NobelGuide TM perfect planning for perfect teeth, procedures & products—Powered by Procera, 2005, Nobel Biocare Services AG, Sweden, pp. 1-44.
Feb. 26, 2016 Office Action issued in U.S. Appl. No. 14/617,327.
Dec. 1, 2016 Office Action Issued in U.S. Appl. No. 14/617,327.
May 18, 2017 US Office Action Issued in U.S. Appl. No. 14/617,327.
Nov. 9, 2017 Office Action issued in U.S. Appl. No. 14/617,327.
Jun. 5, 2018 Office Action Issued in U.S. Appl. No. 14/617,327.
Dec. 4, 2018 Office Action issued in U.S. Appl. No. 14/617,327.
Dec. 20, 2018 Office Action issued in U.S. Appl. No. 15/446,945.
Aug. 27, 2018 Office Action issued in U.S. Appl. No. 15/446,945.
Mar. 13, 2018 Office Action issued in U.S. Appl. No. 15/446,945.
Aug. 10, 2017 Office Action issued in U.S. Appl. No. 15/446,945.

* cited by examiner

FIXATION PIN

This is a Divisional of application Ser. No. 15/446,945 filed Mar. 1, 2017, which in turn is a Divisional of Ser. No. 14/617,327 filed Feb. 9, 2015, which is a Continuation of application Ser. No. 12/627,270 filed Nov. 30, 2009, which claims the benefit of EP 08020837 filed Dec. 1, 2008. The disclosure of the prior applications is hereby incorporated by reference herein in its entirety.

The present invention relates to a fixation pin for a dental template, to a set comprising the fixation pin and to its use for fixing a dental drill template.

In dentistry it is well known to replace either missing teeth or carious teeth where the progress of caries is such that they cannot be fixed in another, less invasive way. Said missing teeth are usually replaced by an endosseous implant with an artificial supra-structure. While quite a lot research was done to improve the dental implants itself, tools and devices which aid in planning the implantation and during the surgical intervention have long been neglected. However in recent years said aiding devices became more and more important.

For instance, the drilling of the hole necessary for the endosseous part of the dental implant has been simplified. While at the beginning the drilling of said hole was purely dependent on the skills of the individual surgeon there are nowadays drill templates which are adapted to the anatomy of the individual patient and which serve to achieve a precise drilling of the holes. The drill template is manufactured after a preceding check of the anatomy of the patient's jaw bone. Such a check helps to define the most optimal position of the necessary bore holes. Once this positional information has been obtained and incorporated into the drill template by means of bore holes, the drill template is used by the surgeon to provide an optimal guiding of the drill thereby achieving the desired axis and dimensions of the hole. The drilling of the holes is a crucial step for a successful implantation, since it is hardly possible to correct wrongly positioned bore holes. Even slight corrections, e.g. of the drill axis, further diminish jaw bone mass and are thus difficult to correct. Although it is of utmost importance that drill templates are kept exactly in position once they have been placed on the jaw or the gum of a patient there are no special means to keep the drill template in place during its use.

Therefore, the problem of the present invention is to provide means for temporarily fixing a drill template in its position while the drill template is used.

The problem is solved by a fixation pin according to claim 1, the set according to claim 13 and the use of the fixation pin according to claim 14. Preferred embodiments are subject to dependent claims.

A fixation pin for fixing a dental drill template according to the present invention has a head which has a bearing surface that is intended to bear at least partially on a drill template or a drill sleeve comprised in the drill template. The fixation pin has further a rod that has a shape of an essentially circular cylinder and which extends from the bearing surface of the head at an essentially right angle, whereby said rod is intended to be inserted into the drill template or the drill sleeve comprised in the drill template.

The fixation pin provides for a fast and reliable fixation of a drill template and is easy to handle. Since the rod of the fixation pin does not have a screw thread there is no screwing requirement. On the contrary, the essentially cylindrical shape of the rod can be easily inserted into the drill template or the drill sleeve comprised in the drill template and ensures a fast and detachable fixation of the drill template. Further, multiple insertion of a rod having a screw thread is likely to damage the bore hole and thus hamper the subsequent insertion of a dental implant such that the implantation is unsuccessful because of poor osseointegration of the implant. The fixation pin also serves as a temporary cap of the bore hole and prevents the intrusion of blood, bone debris and other unwanted particles or liquids (e.g. saliva of the patient). This is particularly advantageous if several holes have to be drilled. Further, the bearing surface of the head of the fixation pin provides a physical stop limiting the depth, the fixation pin may be inserted into drill template or the drill sleeve comprised in the drill template, thereby also limiting the depth by which the fixation pin extends into the bore hole that has been drilled into the jaw bone.

In a further embodiment the head of the fixation pin has a shape of an essentially circular cylinder.

In another embodiment the head has a circumventing indentation, said circumventing indentation has preferably a concave shape. The circumventing indentation provides for a good grip. The good grip avoids unintentional slipping and/or dropping of the fixation pin by the operator.

In a further embodiment of the fixation pin the rod has a first portion which extends from the bearing surface of the head. The rod has, subsequent to the first portion, a second portion, said second portion having a diameter which is smaller than the diameter of the first portion. The second portion is attached to the first portion of the rod.

The axis of the first portion and the second portion of the rod are preferably coaxial.

In a further preferred embodiment the first portion of the rod is connected to the second portion of the rod by an intervening third portion which has a conical shape.

In another embodiment the fixation pin is made of one single piece. Being made of one piece the manufacturing of the fixation pin is simplified and its mechanical stability is further improved.

In a further embodiment the fixation pin is made of a material which is selected from the group that consists of hard plastics, stainless steel, titanium and titanium alloys.

In a preferred embodiment the fixation pin is made of titanium or a titanium alloy. Titanium has a very good stability and is biologically inert, that is to say, it has an excellent biocompatibility.

In a further embodiment the fixation pin is made of stainless steel. The material stainless steel is most preferred. Stainless steel shows also a very good stability and is biologically inert. Stainless steel is readily available and is inexpensive.

In another embodiment the fixation pin further comprises an aspiration security. Said aspiration security prevents unwanted aspiration of the fixation pin by the patient. Such an unwanted aspiration may be harmful for the patient and cause injury.

In a preferred embodiment the aspiration security is a string that is attached to the head of the fixation pin. For instance, a dental floss may be bound around the head of the fixation pin, more precisely, around the circumventing indentation.

While the fixation pin is inserted in the drill template or the sleeve comprised in the drill template in a patients mouth, the end of the string which is opposite to the one attached to the fixation pin may be temporarily fixed outside the mouth of the patient. It may also be simply held by hand.

The present invention also relates to a set that comprises at least one fixation pin according to the present invention. Preferably, the set comprises more than one fixation pin according to the present invention, whereby at least some of the fixation pins differ in their diameter. Differing in their diameter means that the fixation pins have either different diameters in the second portion of the rod and the same diameter in the first portion or they differ in the diameter of the first portion, whereas the diameter of the second portion is the same. It is also possible that the fixation pins comprised in the set differ in the diameter of the first portion of the rod and the second portion of the rod.

The present invention relates also to the use of a fixation pin according to the present invention for fixing a drill template. The fixation pin provides for a simple and secure fixation of a drill template. Its use is particularly advantageous for fixing drill templates which have at least two bore holes.

The fixation pin according to the present invention will be explained in more detail in the following text with reference to exemplary embodiments, which are illustrated in the drawings and in which, purely schematically:

Figure 1:
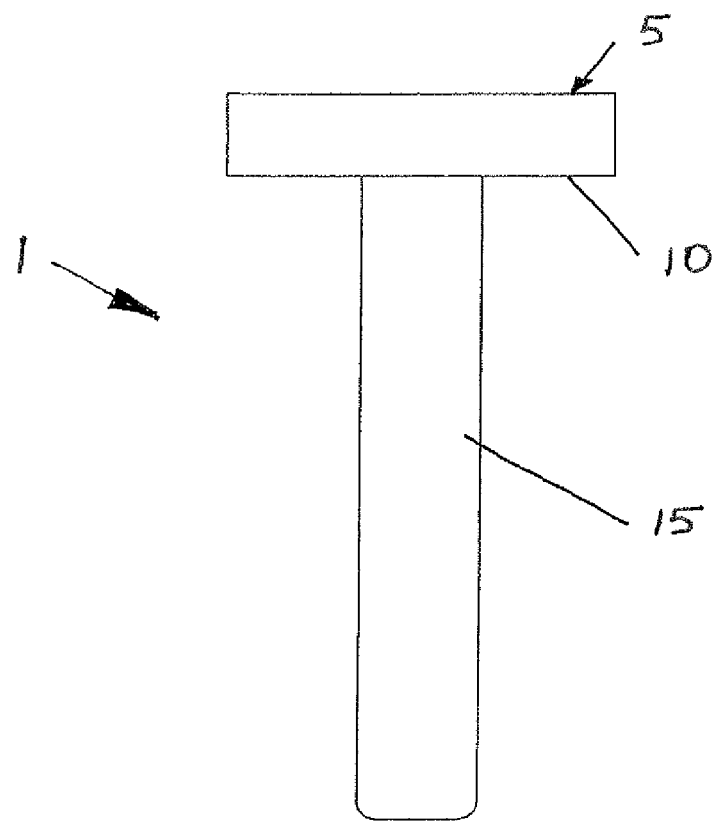
FIG. 1 shows a first embodiment of the fixation pin in a longitudinal section.

FIG. 1 shows a first embodiment of the fixation pin in a longitudinal section. The fixation pin 1 has a head 5 which has a bearing surface 10. From the bearing surface 10 a rod 15 extends at an essentially right angle. The rod 15 has a shape of an essentially circular cylinder and its diameter is constant throughout the length of the rod. The rod 15 is arranged in the centre of the bearing surface 10.

Figure 2:
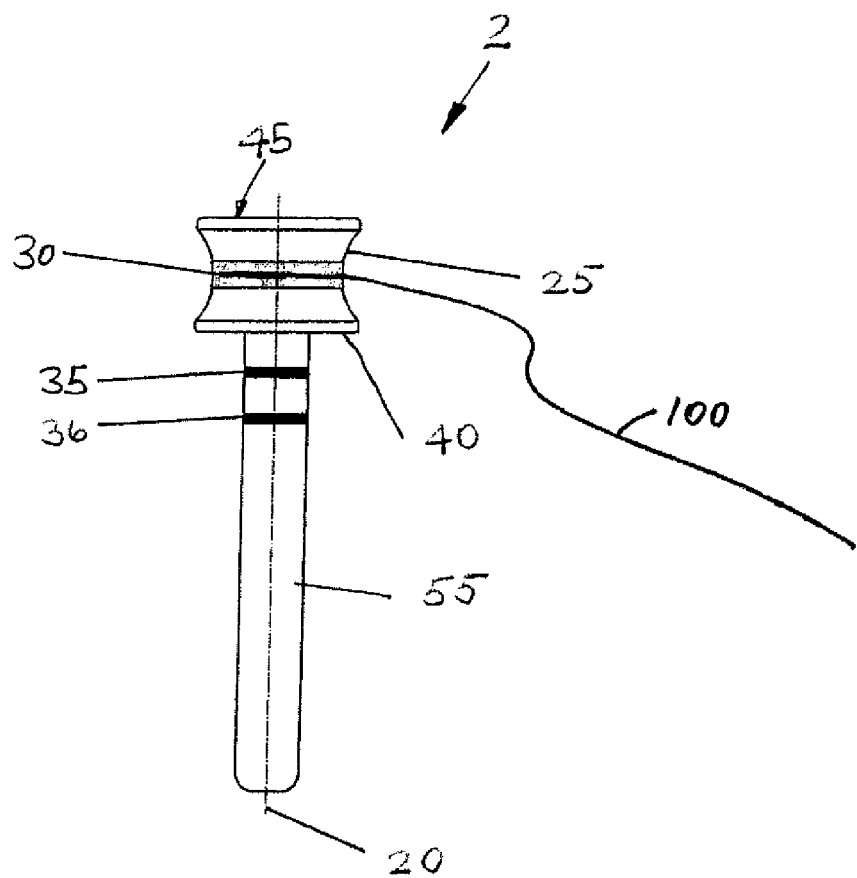
FIG. 2 shows a second embodiment of the fixation pin in a profile view.

FIG. 2 shows a preferred embodiment of the fixation pin according to the present invention. The fixation pin 2 has a head 45 which has a shape of an essentially circular cylinder. From the bearing surface 40 of the head 45 extends a rod 55 that also has a shape of an essentially circular cylinder. The head 45 and the rod 55 are coaxially arranged and have a common axis 20. Further, the head 45 has a circumventing indentation 25 having in a concave shape. The head 45 also carries a mark in the form of a coloured, circumventing band 30. Said coloured circumventing band serves as a colour code for distinguishing different sets of fixation pins. The colour code may, for instance, refer to the diameter of the bore hole. Since different dental implants require bore holes of different diameter, fixation pins whereby the portion intended to be inserted into the bore hole meets this requirement, are also needed. The colour code allows for an easy distinction of the different fixation pins. In addition, the rod carries two height marks 35, 36 indicating different heights or distances. These marks provide visible stop marks that allow the surgeon to insert the fixation pin to a certain depth into the drill template or the drill sleeve comprised in the drill template and the bore hole. The maximum depth, that a fixation pin can be inserted is limited by the bearing surface of the head of the fixation pin, thereby providing a physical stop.

Figure 3:
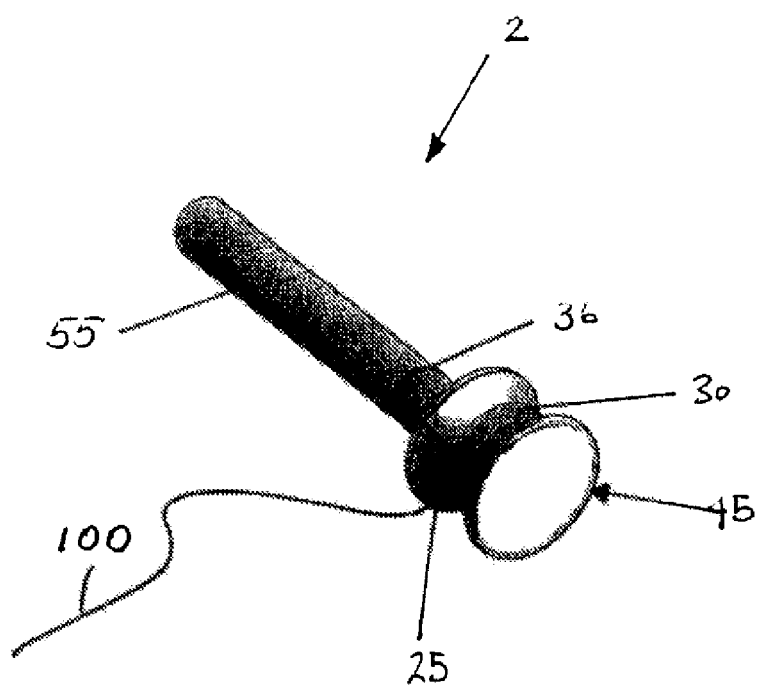
FIG. 3 shows the fixation pin according to FIG. 2 in a perspective view.

FIG. 3 shows the fixation pin of FIG. 2 in a perspective view. The fixation pin 2 which has a head 45 having a circumventing indentation 25 of an essentially concave shape. In the concave indentation 25 the coloured, circumventing band 30 is shown. A rod 55 extends in coaxial direction from the head 45. Said rod carries height marks 35, 36 of which only one can be seen.

Figure 4:
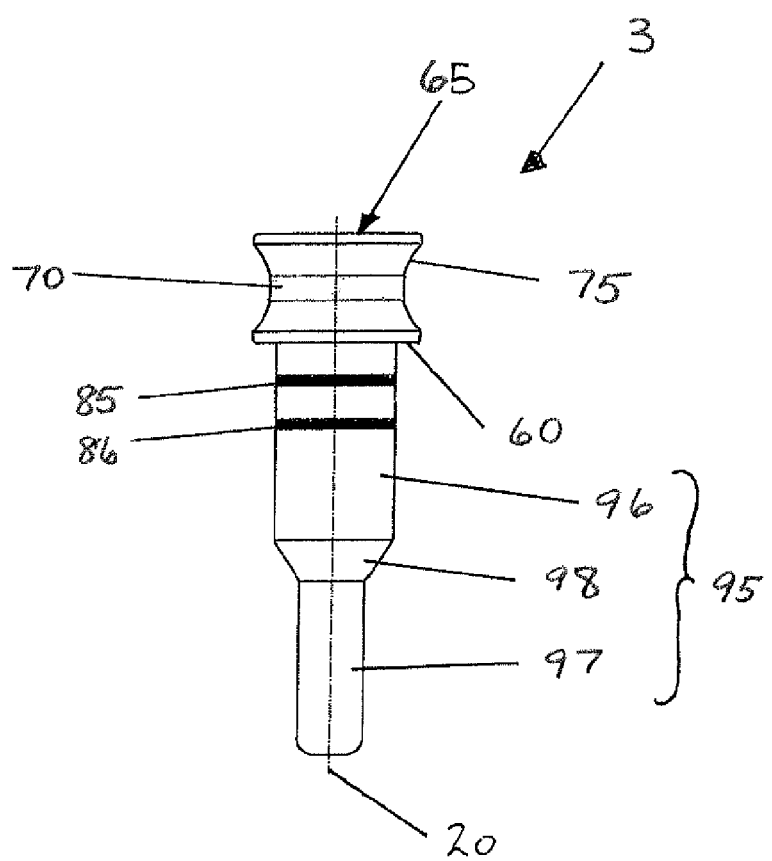
FIG. 4 shows a further embodiment of the fixation pin in a profile view.

As illustrated in FIGS. 2 and 3, the fixation pin may also comprise an aspiration security 100. Said aspiration security 100 prevents unwanted aspiration of the fixation pin by the patient. Such an unwanted aspiration may be harmful for the patient and cause injury. The aspiration security 100 may be a string that is attached to the head of the fixation pin, as shown in FIGS. 2 and 3. For instance, a dental floss may be bound around the head of the fixation pin, more precisely, around the circumventing indentation FIG. 4 shows a further embodiment of the fixation pin. The fixation pin 3 with a head 65 having a bearing surface 60 from which a rod 95 coaxially extends in direction of the common axis 20. The head 65 has a circumventing indentation 75 with a coloured, circumventing band 70. The rod 95 has a first portion 96 extending from the bearing surface 60 and a second portion 97 that has a smaller diameter than the diameter of the first portion 96. The first portion 96 of the rod 95 is connected to the second portion 97 by an intervening third portion 98 which third portion has a conical shape. The height marks 85, 86 are arranged on the first portion 96 of the rod 95.

Figure 5:
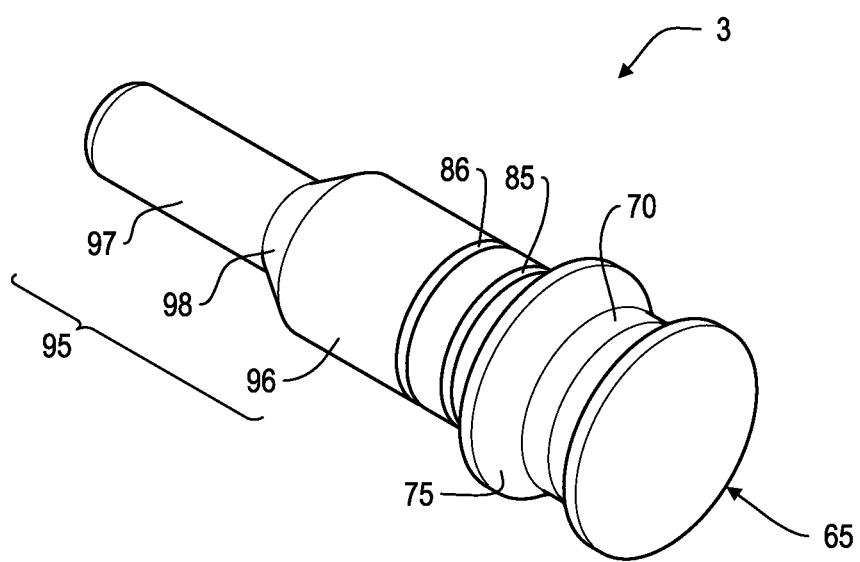
FIG. 5 shows the fixation pin according to FIG. 4 in a perspective view.

FIG. 5 shows the fixation pin of FIG. 4 in a perspective view. The fixation pin 3 has a head 65 having a circumventing indentation 75 and a coloured, circumventing band 70. From a bearing surface of the head 65 which cannot be seen in this view a rod 95 extends at an essentially right angle. The rod 95 has three different portions 96, 97, and 98. While the first portion 96 extends from said bearing surface of the head 65, the second portion 97 of the rod 95 is connected to the first portion 96 by an intervening portion 98 which has a conical shape. The second portion 97 has a diameter that is smaller than the diameter of the first portion 96. The intervening portion 98 has two end faces with different diameters. The end face of the intervening portion 98 with the smaller diameter adjoins the second portion 97 of the rod 95, whereas the end face of the intervening portion 98 having the greater diameter adjoins the first portion 96 of the rod 95.

The invention claimed is:

1. A fixation pin for fixing a dental drill template, the fixation pin comprising:

a head having a shape of an essentially circular cylinder, the head comprising:
  a first, free end and a second end in an axial direction of the head,
  a bearing surface at the second end of the head that is configured to bear at least partially on the drill template or a sleeve provided in the drill template,
  an upper surface at the first, free end of the head opposite to the bearing surface, the upper surface being continuous, and
  a peripheral indentation formed around an outer circumferential surface of the head between the bearing surface and the upper surface of the head, the peripheral indentation connecting the first, free end and the second end of the head and forming in the axial direction of the head a continuous concave-shaped curve that extends from the first, free end of the head to the second end of the head;

a rod having a shape of an essentially circular cylinder, the rod having a length that extends between a first rod end at the bearing surface and a second, free rod end, the rod extending from the bearing surface of the head at an essentially right angle, the rod being configured to be inserted into the drill template or the sleeve provided in the drill template and into a bore hole formed in a jaw bone, the rod having a cylindrical outer surface from the first rod end to the second rod end, and the rod having a diameter that is constant along the length of the rod between the first rod end and the second, free rod end, the second, free rod end being a rounded free end, the diameter of the rod being configured to correspond to a diameter of the bore hole; and an aspiration security member, wherein a diameter of the head at the bearing surface is larger than the diameter of the rod.

2. The fixation pin according to claim 1, wherein the peripheral indentation has a concave shape.

3. The fixation pin according to claim 1, wherein the fixation pin is made of one single piece.

4. The fixation pin according to claim 1, wherein the fixation pin is made of a material selected from the group consisting of hard plastics, stainless steel, titanium, and titanium alloys.

5. The fixation pin according to claim 4, wherein the fixation pin is made of a material selected from the group consisting of titanium and titanium alloys.

6. The fixation pin according to claim 4, wherein the fixation pin is made of stainless steel.

7. The fixation pin according to claim 1, wherein the aspiration security member is a string attached to the head of the fixation pin.

8. A set comprising two or more of the fixation pins according to claim 1.

9. The set according to claim 8, wherein at least one of the two or
more fixation pins has a diameter different from another one of the two or more fixation pins.

10. The fixation pin according to claim 1, wherein the head includes a mark indicating the diameter of the bore hole that corresponds to the diameter of the rod.

* * * * *